(12) United States Patent
Crouch et al.

(10) Patent No.: US 12,194,181 B2
(45) Date of Patent: Jan. 14, 2025

(54) CONTAINMENT VESSELS FOR RAPID THERMO-CHEMICAL DECONTAMINATION OF FACEMASKS OR OTHER PERSONAL PROTECTION EQUIPMENT (PPE)

(71) Applicant: Raytheon Company, Waltham, MA (US)

(72) Inventors: David D. Crouch, Riverside, CA (US); Alf L. Carroll, III, Marion, MA (US); John Carcone, Portsmouth, RI (US); David R. Sar, Marana, AZ (US); Travis B. Feenstra, Calimesa, CA (US)

(73) Assignee: Raytheon Company, Tewksbury, MA (US)

( * ) Notice: Subject to any disclaimer, the term of this patent is extended or adjusted under 35 U.S.C. 154(b) by 308 days.

(21) Appl. No.: 16/944,617

(22) Filed: Jul. 31, 2020

(65) Prior Publication Data
US 2021/0330841 A1    Oct. 28, 2021

Related U.S. Application Data

(60) Provisional application No. 63/015,000, filed on Apr. 24, 2020.

(51) Int. Cl.
*A61L 2/20*   (2006.01)
*A61L 2/07*   (2006.01)
*A61L 2/26*   (2006.01)

(52) U.S. Cl.
CPC ............... *A61L 2/208* (2013.01); *A61L 2/07* (2013.01); *A61L 2/26* (2013.01); *A61L 2202/11* (2013.01);
(Continued)

(58) Field of Classification Search
CPC ....... A61L 2/208; A61L 2/07; A61L 2202/121
See application file for complete search history.

(56) References Cited

U.S. PATENT DOCUMENTS

| 3,988,930 A | 11/1976 | Fitzmayer et al. |
| 4,861,956 A | 8/1989 | Courneya |
| (Continued) | | |

FOREIGN PATENT DOCUMENTS

| CN | 108480290 A | 9/2018 |
| CN | 108743997 A | 11/2018 |
| (Continued) | | |

OTHER PUBLICATIONS

Thekombuchacompany, Step 5—IBC Rainwater Harvesting System—Connecting and Venting Tanks, Oct. 2014, YouTube, https://www.youtube.com/watch?v=9xj-Fus7R7Q (Year: 2014).*
(Continued)

*Primary Examiner* — Sean E Conley

(57) ABSTRACT

An apparatus includes a containment vessel having an interior space configured to be sealed. The interior space is configured to receive at least one reservoir of liquid to be vaporized during a decontamination process. The apparatus also includes a base configured to be inserted into the interior space. The base is configured to receive one or more pieces of personal protection equipment to be heated and decontaminated within the interior space during the decontamination process. The base is configured to hold the one or more pieces of personal protection equipment above the at least one reservoir of liquid. The apparatus further includes a pressure-relief valve configured to be opened to release a pressure within the interior space. In some cases, the apparatus may include a filter configured to filter material passing through the pressure-relief valve.

20 Claims, 8 Drawing Sheets

(52) U.S. Cl.
CPC ... *A61L 2202/121* (2013.01); *A61L 2202/122* (2013.01); *A61L 2202/26* (2013.01)

(56) References Cited

U.S. PATENT DOCUMENTS

| | | | |
|---|---|---|---|
| 5,108,701 A * | 4/1992 | Zakaria | A61L 2/0011 219/754 |
| 5,117,809 A | 6/1992 | Scaringe et al. | |
| 8,802,023 B1 * | 8/2014 | Lewis | A61L 2/00 422/305 |
| 9,222,665 B2 | 12/2015 | Halas et al. | |
| 9,878,061 B2 | 1/2018 | Shur et al. | |
| 10,654,726 B2 | 5/2020 | Nigrelli | |
| 11,612,668 B2 | 3/2023 | Crouch et al. | |
| 2001/0036670 A1 | 11/2001 | Fryer et al. | |
| 2003/0206827 A1 | 11/2003 | Lin et al. | |
| 2004/0040586 A1 | 3/2004 | Kumar | |
| 2007/0186579 A1 * | 8/2007 | Barker | F25D 3/08 62/457.2 |
| 2007/0253859 A1 * | 11/2007 | Hill | A61L 9/22 422/3 |
| 2008/0251063 A1 | 10/2008 | Palena et al. | |
| 2013/0280134 A1 | 10/2013 | Hoffman et al. | |
| 2014/0224687 A1 | 8/2014 | Schuster | |
| 2016/0264332 A1 | 9/2016 | Rapparini et al. | |
| 2016/0352022 A1 | 12/2016 | Thomson et al. | |
| 2018/0140732 A1 * | 5/2018 | Liu | A46B 17/065 |
| 2022/0184256 A1 | 6/2022 | Crouch et al. | |
| 2022/0265880 A1 | 8/2022 | Feenstra et al. | |

FOREIGN PATENT DOCUMENTS

| | | |
|---|---|---|
| CN | 109959175 A | 7/2019 |
| CN | 111012933 A | 4/2020 |
| GB | 2507724 A | 5/2014 |
| WO | 2017223224 A1 | 12/2017 |

OTHER PUBLICATIONS

International Search Report and Written Opinion of the International Searching Authority in connection with International Patent Application No. PCT/US2021/070215 issued Jun. 15, 2021, 10 pages.

Heimbuch et al., "A Pandemic Influenza Preparedness Study: Use of Energetic Methods to Decontaminate Filtering Facepiece Respirators Contaminated with H1N1 Aerosols and Droplets", Jun. 2012, 11 pages.

"Bioquell | Clarus C", Product Sheet, Bioquell UK Ltd., 2012, 2 pages.

Lowe et al., "N95 Filtering Facepiece Respirator Ultraviolet Germicidal Irradiation (UVGI) Process for Decontamination and Reuse", Nebraska Medicine, Apr. 2020, 19 pages.

Carlson et al., "Solar powered water purification system," Mechanical Engineering Senior Theses, Santa Clara University, Jan. 2012, 160 pages.

Chandler, "Sterilizing with the sun: Solar concentrating system could replace fuel-powered or electric devices in remote villages," Phys.org News, Feb. 2013, 3 pages.

"Food Cooking Medical Sterilization and Ice Making (adsorption process) with the Soleil-Vapeur Solar Thermal Steam Unit," soleil-vapeur.org, Oct. 2014, 4 pages.

Lu, "Portable device uses solar power to sterilise medical equipment," NewScientist, Nov. 2020, 6 pages.

Mechler, "Mask Disinfection & Sterilization for Viruses," https://consteril.com/covid-19-pandemic-disinfection-and-sterilization-of-face-masks-for-viruses, Apr. 2020, 19 pages.

"Parabolic Solar Trough—Thermal Water Heater," Parabolic Trough Concentrated Solar Power, Dec. 2020, 6 pages.

"Preppers Peak Solar Cooker Kettle for Camping Outdoor Travel with Solar Technology," Kettles for Water, Dec. 2020, 2 pages.

Roel, "350mm f/4 lightweight truss Dobson (airline transportable)," DIY Astronomer, Stargazers Lounge, Dec. 2013, 23 pages.

Sherwin, "GoSun Sport: Portable, High Efficiency Solar Cooker," Kickstarter, May 2019, 29 pages.

"Sterilizing medical tools off the grid using solar heat," Innovation Toronto, Dec. 2020, 5 pages.

U.S. Department of Labor, "Hospital Respiratory Protection Program Toolkit Resources for Respirator Program Administrators," Occupational Safety and Health Administration (OSHA), DHHS (NIOSH) Publication Number 2015-117, OSHA Publication No. 3767, May 2015, 96 pages.

Non-Final Office Action dated Mar. 15, 2023 in connection with U.S. Appl. No. 17/169,260, 13 pages.

Final Office Action dated Sep. 27, 2023 in connection with U.S. Appl. No. 17/169,260, 15 pages.

Non-Final Office Action dated Mar. 20, 2024 in connection with U.S. Appl. No. 17/169,260, 15 pages.

Non-Final Office Action dated Sep. 17, 2024 in connection with U.S. Appl. No. 17/169,260, 9 pages.

Communication pursuant to Article 94(3) EPC dated Oct. 28, 2024 in connection with European Patent Application No. 21714604.2, 3 pages.

* cited by examiner

CONTAINMENT VESSELS FOR RAPID THERMO-CHEMICAL DECONTAMINATION OF FACEMASKS OR OTHER PERSONAL PROTECTION EQUIPMENT (PPE)

CROSS-REFERENCE TO RELATED APPLICATION AND PRIORITY CLAIM

This application claims priority under 35 U.S.C. § 119(e) to U.S. Provisional Patent Application No. 63/015,000 filed on Apr. 24, 2020, which is hereby incorporated by reference in its entirety.

TECHNICAL FIELD

This disclosure relates generally to medical decontamination devices and processes. More specifically, this disclosure relates to containment vessels for rapid thermo-chemical decontamination of facemasks or other personal protection equipment (PPE).

BACKGROUND

A dangerous gap has developed in the available supply of disposable facemasks, such as N95/N99/N100/P100 surgical masks, and other personal protection equipment (PPE), such as surgical gowns and booties, as a result of the COVID-19 pandemic. Accelerating demand has outstripped the ability of the supply chain to keep pace. As a result, medical staff are (among other things) routinely forced to wear the same mask or other personal protection equipment to treat multiple patients, which poses a cross-contamination hazard to patients and medical personnel. An additional risk is mask "breakthrough" in which contaminants eventually diffuse through the mask and infect the wearer.

SUMMARY

This disclosure provides containment vessels for rapid thermo-chemical decontamination of facemasks or other personal protection equipment (PPE).

In a first embodiment, an apparatus includes a containment vessel having an interior space configured to be sealed. The interior space is configured to receive at least one reservoir of liquid to be vaporized during a decontamination process. The apparatus also includes a base configured to be inserted into the interior space. The base is configured to receive one or more pieces of personal protection equipment to be heated and decontaminated within the interior space during the decontamination process. The base is configured to hold the one or more pieces of personal protection equipment above the at least one reservoir of liquid. The apparatus further includes a pressure-relief valve configured to be opened to release a pressure within the interior space.

In a second embodiment, a method includes placing at least one reservoir of liquid to be vaporized during a decontamination process in an interior space of a containment vessel. The method also includes placing one or more pieces of personal protection equipment within the interior space of the containment vessel on a base, where the base is configured to hold the one or more pieces of personal protection equipment above the at least one reservoir of liquid. The method further includes sealing the interior space of the containment vessel and decontaminating the one or more pieces of personal protection equipment by heating the one or more pieces of personal protection equipment in the sealed interior space of the containment vessel. In addition, the method includes opening a pressure-relief valve of the containment vessel after decontaminating the one or more pieces of personal protection equipment.

Other technical features may be readily apparent to one skilled in the art from the following figures, descriptions, and claims.

BRIEF DESCRIPTION OF THE DRAWINGS

For a more complete understanding of this disclosure, reference is made to the following description, taken in conjunction with the accompanying drawings, in which.

DETAILED DESCRIPTION

Figure 1:
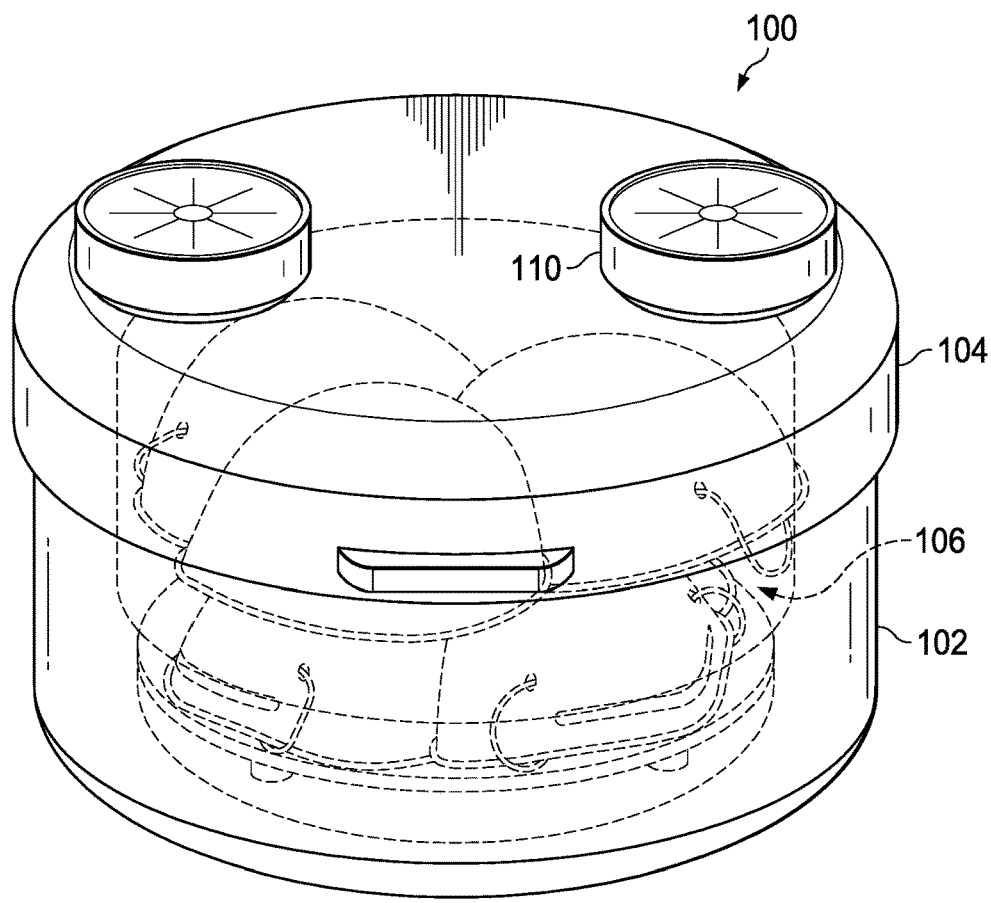
FIGS. 1 through 4 illustrate a first example containment vessel for rapid thermo-chemical decontamination of facemasks or other personal protection equipment (PPE) in accordance with this disclosure.

FIGS. 1 through 15, described below, and the various embodiments used to describe the principles of the present disclosure are by way of illustration only and should not be construed in any way to limit the scope of the disclosure. Those skilled in the art will understand that the principles of the present disclosure may be implemented in any type of suitably arranged device or system.

As noted above, a dangerous gap has developed in the available supply of personal protection equipment (PPE), such as disposable facemasks (like N95/N99/N100/P100 surgical masks), surgical gowns, and booties, as a result of the COVID-19 pandemic. Disposable facemasks are sometimes referred to as surgical respirators. Accelerating demand has outstripped the ability of the supply chain to keep pace. As a result, medical staff are (among other things) routinely forced to wear the same mask or other personal protection equipment to treat multiple patients. This poses a cross-contamination hazard to patients and medical personnel and poses an additional risk related to mask "breakthrough" in which contaminants eventually diffuse through the mask and infect the wearer. Under normal circumstances, facemasks, surgical gowns, booties, and other personal protection equipment may typically be disposable, meaning they are worn once and discarded. However, when supplies run low (such as during a pandemic), it may be necessary or desirable to decontaminate and reuse facemasks, surgical gowns, booties, and other personal protection equipment.

Some approaches for decontaminating personal protection equipment involve the use of hydrogen peroxide ($H_2O_2$) vapor to decontaminate the equipment. However, these approaches may take an extended period of time (such as about 8 hours) to complete, which can be problematic in environments where a large amount of personal protection equipment is used. These approaches may also require high concentrations of hydrogen peroxide (such as 35% compared to about 3% to 6% over-the-counter solutions), which can be toxic and potentially explosive. Other approaches for decontaminating personal protection equipment involve the use of ultraviolet germicidal irradiation in which the equipment is illuminated using ultraviolet light, which can deactivate or kill bacteria and viruses. However, inner layers of a facemask or other personal protection equipment may not receive a high enough dose of ultraviolet radiation, and light transmittance varies among equipment. Also, straps or other structures of personal protection equipment can present a residual contamination risk and may require a secondary decontamination process, and it is often challenging to ensure that all surfaces/layers of personal protection equipment are completely decontaminated due to shadowing effects. Still other approaches for decontaminating personal protection equipment involve the use of microwave-generated steam, which is an effective technique for decontaminating medical instruments and other materials used every day in surgeries, procedures, and patient services. However, when used with disposable personal protection equipment, microwave-generated steam runs the risk of overheating the equipment, causing damage or degradation. If a facemask is even slightly deformed by heating to excessive temperatures, it can lose its ability to protect the wearer and must be discarded.

This disclosure provides various containment vessels for rapid thermo-chemical decontamination of facemasks or other personal protection equipment. These containment vessels can be used in a decontamination process, such as one that uses heating in combination with a low-concentration hydrogen peroxide solution, to rapidly decontaminate personal protection equipment in order to facilitate safe reuse of the equipment, such as during pandemic-induced shortages. Heating can be achieved using a microwave, stovetop, oven, or other heat source. Also, low-concentration hydrogen peroxide solutions (such as about 3% to 6%) are routinely available in a medical setting (such as a standard hospital or a mobile Army surgical hospital (MASH) setting) or in a commercial setting (such as a pharmacy or grocery store). Thus, various equipment and chemicals used to support the decontamination process are typically already available in the setting and can be used here. Moreover, as described below, peak temperatures experienced by the personal protection equipment during the decontamination process can be limited to a suitable range, such as about 65° C. to about 80° C., which prevents damage to the equipment or degradation of the equipment's fit or function. In addition, the use of the containment vessels, such as one with a HEPA filter or other filter, may present little or no hazard to medical staff.

In some embodiments, the process for decontaminating facemasks or other personal protection equipment involves placing the personal protection equipment within a containment vessel. The containment vessel includes at least one reservoir of a low-concentration hydrogen peroxide solution, such as an about 3% to about 6% hydrogen peroxide solution or other hydrogen peroxide solution that is safe for everyday use. The at least one reservoir can be positioned under the personal protection equipment to help provide adequate vapor in the containment vessel and around the personal protection equipment during decontamination. The personal protection equipment may also be soaked in the low-concentration hydrogen peroxide solution prior to placement in the containment vessel. The containment vessel can be initially heated and then sealed in order to keep moisture, hydrogen peroxide, and contaminants inside the containment vessel during the decontamination process. The containment vessel is heated to a raised temperature, such as about 65° C. to about 80° C. (like about 70° C.), and maintained at the raised temperature for a relatively short period of time (like about five minutes to about ten minutes) to decontaminate the personal protection equipment inside the containment vessel. The containment vessel can be heated using a microwave, stovetop, or oven, via solar radiation, or in any other suitable manner. However heated, the combination of heat and heat-activated hydrogen peroxide deactivates or destroys biocontaminants faster and at a lower temperature than either heat or hydrogen peroxide vapor alone. Once the decontamination cycle is complete, the personal protection equipment can be dried (inside or outside the containment vessel) and then used as needed.

In this way, synergy is achieved by attacking contaminants with both moist heating and hydrogen peroxide, yielding faster and more effective decontamination than either approach used alone. Also, the lower-temperature decontamination process protects facemasks or other personal protection equipment from damage or degradation, and the use of materials such as about 3% to about 6% hydrogen peroxide solution avoids toxic concentrations and potential explosiveness of higher concentrations. Moreover, the presence of metal nose strips, staples, or other metal components of the personal protection equipment will not cause damage to the equipment or their rubber straps during the decontamination process. This may be achieved using lower-power operation (to limit temperature increases) and the presence of moisture in the containment vessels, which helps to prevent the metal components from overheating and damaging the personal protection equipment. This may also be achieved by distributing and orienting the personal protection equipment to reduce or minimize the risk of arcing between metal components while increasing or maximizing the number or amount of equipment that can fit into the available volume (to reduce or minimize the decontamination cost per piece of equipment). Further, a containment vessel (such as one with at least one pressure-relief valve) may optionally facilitate a multi-stage process, namely (i) a first stage where the pressure-relief valve is opened and where the containment vessel is heated so air within the containment vessel is substantially replaced by vapor, (ii) a second stage where the pressure-relief valve is closed, the containment vessel is sealed and heated, and water and hydrogen peroxide remain inside the containment vessel to maximize the speed and effectiveness of the decontamination, and (iii) a third stage where the pressure-relief valve is opened and where the containment vessel is heated so that water vapor and other vapor can escape while the personal protection equipment dries inside the containment vessel. This facilitates separate decontamination and drying operations, where water and hydrogen peroxide are retained during the decontamination and allowed to escape during the drying. In addition, at least one HEPA filter or other filter can be placed at the outlet(s) of the pressure-relief valve(s) or other outlet(s) of the containment vessel as an added precaution if necessary or desirable.

Figure 2:
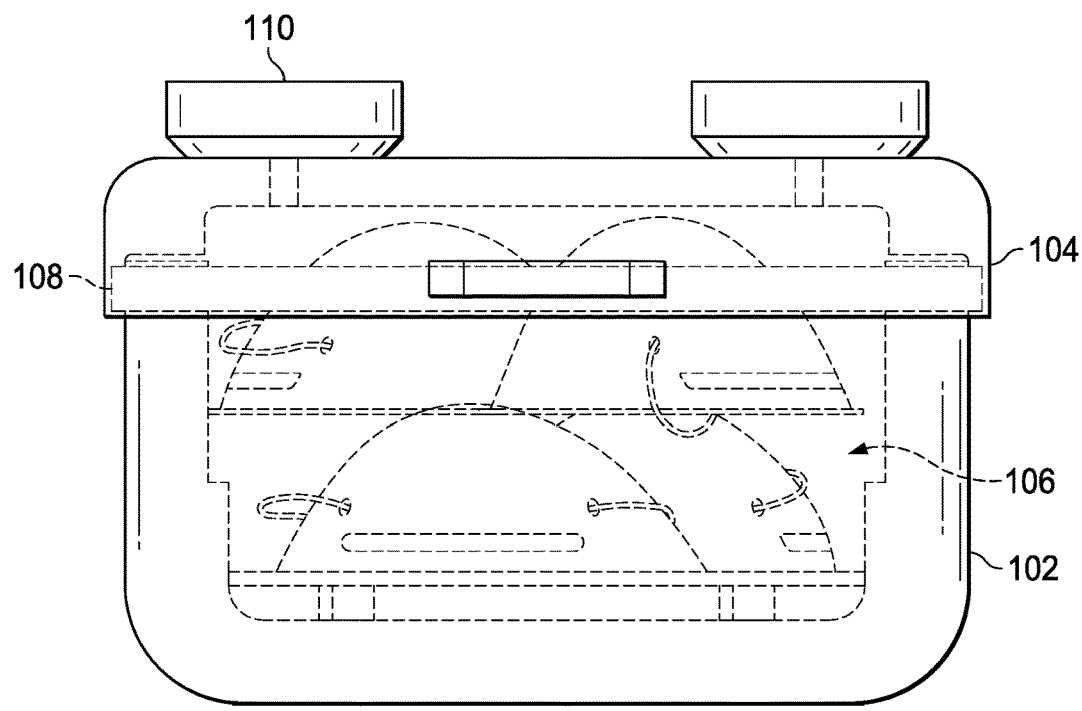

FIGS. 1 through 4 illustrate a first example containment vessel 100 for rapid thermo-chemical decontamination of facemasks or other personal protection equipment in accordance with this disclosure. As shown in FIGS. 1 and 2, the containment vessel 100 generally takes the form of a modified, customized, or other microwavable pressure cooker or similar type of device. In this example, the containment vessel 100 includes a body 102 and a lid 104 configured to be secured to the body 102. The body 102 and lid 104 collectively define an interior space or volume 106 into which personal protection equipment can be placed. A seal 108 may be positioned between the body 102 and the lid 104 in order to help isolate or seal the volume 106 when the lid 104 is secured to the body 102. This helps to retain water, hydrogen peroxide, contaminants, or other materials inside the containment vessel 100 until a decontamination process is completed.

The body 102 and lid 104 of the containment vessel 100 may be formed from any suitable material(s). In some embodiments, the body 102 and lid 104 may be formed from ruggedized plastic or other material(s) that can be used in a microwave. This may include one or more materials having a low loss tangent at 915 MHz and/or 2.45 GHz and a suitable glass transition or softening temperature, such as high-density polyethylene, polymethylpentene, polypropylene, or polysulfone. Other materials may include those normally used in food preparation, such as metal, tempered glass, or ceramic. The body 102 and lid 104 may also be formed in any suitable manner, such as additive manufacturing, injection molding, casting, machining, or other suitable technique. The containment vessel 100 overall may have any suitable size, shape, and dimensions, and each of the body 102 and lid 104 may have any suitable size, shape, and dimensions. As a particular example, the containment vessel 100 may have an internal volume 106 of about 3.4 quarts, a height of about 7.75 inches, and a generally cylindrical shape, although other capacities, sizes, and shapes may be used. In some cases, the body 102 and lid 104 may represent interlocking portions such that the lid 104 can be mechanically coupled to and released from the body 102, such as via rotation of the lid 104. The seal 108 includes any suitable structure configured to seal the interior space of the containment vessel 100, such as a rubber or other O-ring.

One or more integrated filters and pressure-relief valves 110 can be used with the containment vessel 100. Each pressure-relief valve includes any suitable structure configured to be selectively opened and closed to provide or block a pathway for pressure to escape from the interior volume 106 of the containment vessel 100. Each filter may be used to filter air or other fluid passing out of the containment vessel 100, such as during or after heating of the containment vessel 100. For instance, after being placed in a microwave or otherwise heated for a specified period of time, the pressure-relief valve(s) may be opened, and the filter(s) may filter air passing out of the containment vessel 100. Among other things, this may help to prevent contamination of a microwave, stovetop, oven, or other components used with or around the containment vessel 100. Each filter includes any suitable structure configured to remove contaminants or other materials from fluid, such as a HEPA filter. In some embodiments, each filter is implemented by bonding or otherwise securing an adapter to the containment vessel 100, where the adapter is configured to receive a HEPA or other filter canister. As a particular example, the adapter may be threaded for attachment to the containment vessel 100, and an O-ring or other seal can be used to seal the adapter to the containment vessel 100.

Note that this example includes two integrated filters and pressure-relief valves 110, although the containment vessel 100 may include one or more than two integrated filters and pressure-relief valves 110. Also note that the one or more integrated filters and pressure-relief valves 110 may be positioned at any suitable location(s) of the containment vessel 100 and may or may not be positioned on the lid 104. Further note that the use of integrated filters and pressure-relief valves is not required and that, for instance, at least one pressure-relief valve and at least one separate filter may be used (or the filter or filters may be omitted completely).

Figure 3:
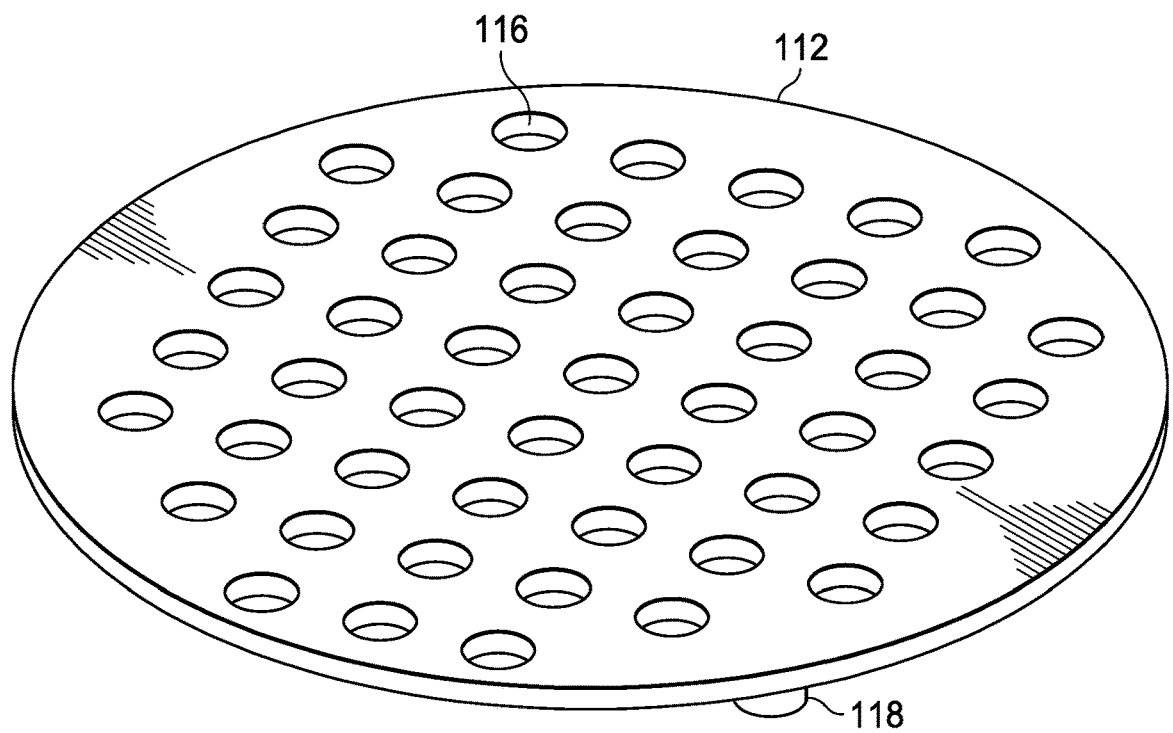
Figure 4:
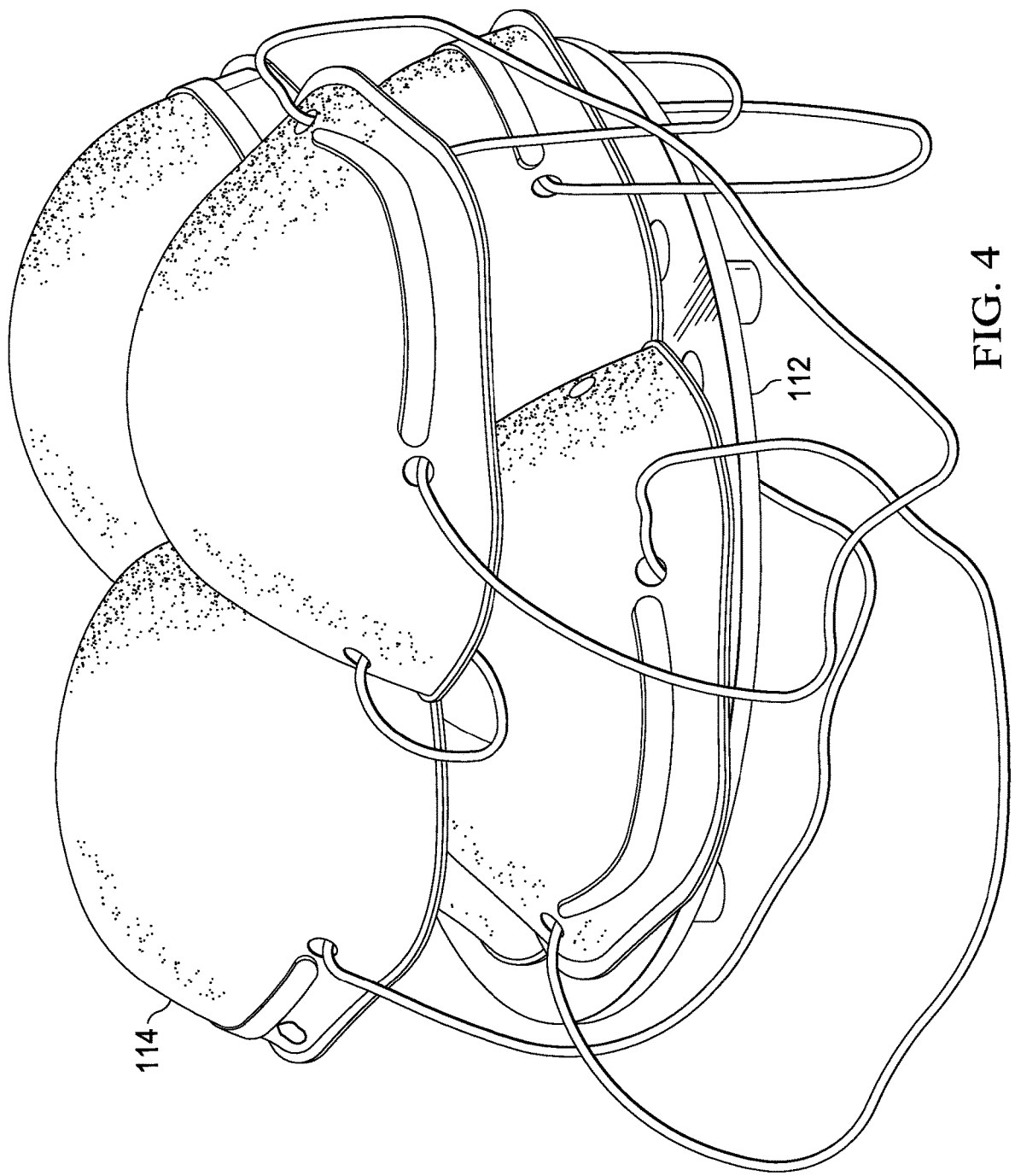

As shown in FIGS. 3 and 4, a base 112 is sized and shaped to fit within the internal volume 106 in the containment vessel 100. One or more pieces of personal protection equipment 114 can be placed on the base 112, and the base 112 holds the personal protection equipment 114 above a bottom surface of the internal volume 106. This allows a reservoir of liquid (such as a low-concentration hydrogen peroxide solution) to be placed within the internal volume 106 of the containment vessel 100 and remain underneath the base 112. When the reservoir of liquid is heated, vaporized liquid can travel upward and surround the personal protection equipment 114 to facilitate decontamination of the personal protection equipment 114. In this example, the base 112 includes multiple holes 116 and multiple standoffs 118. The holes 116 allow vaporized liquid (such as hydrogen peroxide vapor) to travel from under the base 112 to surround the personal protection equipment 114 during the decontamination process. The standoffs 118 elevate or help to hold the base 112 above the bottom surface of the internal volume 106 to provide space for the reservoir of liquid.

The base 112 may be formed from any suitable material(s), such as metal or ruggedized plastic. The base 112 may also be formed in any suitable manner, such as additive manufacturing, injection molding, casting, machining, or other suitable technique. The base 112 may have any suitable size, shape, and dimensions. In this example, the base 112 is generally circular, although other shapes may be used. Each of the holes 116 may have any suitable size, shape, and dimensions, and any suitable number and arrangement of the holes 116 may be used in the base 112. The holes 116 may also be formed in the base 112 in any suitable manner, such as by etching or otherwise forming the holes 116 in an already-formed base 112 or by forming the base 112 to include the holes 116. The standoffs 118 can be formed from any suitable material(s) and in any suitable manner. The standoffs 118 may be formed integral with the base 112 or formed separate from and attached to the base 112.

In this example, the pieces of personal protection equipment 114 include multiple facemasks, such as N95, N99, N100, or P100 surgical masks. In this particular example, six facemasks have been stacked in order to more completely fill the interior volume 106 of the containment vessel 100. However, this stacking may not be required, such as when the containment vessel 100 is wider with a smaller height. Whether stacked or not, the presence of the liquid reservoir (such as a reservoir of low-concentration hydrogen peroxide solution) under the base 112 allows vapor to form and travel through the holes 116 of the base 112 and surround the facemasks. The heating of the interior volume 106 of the containment vessel 100, along with the presence of the vaporized liquid around the personal protection equipment 114, helps to facilitate faster and more effective decontamination of the personal protection equipment 114.

In some embodiments, a decontamination process involving the containment vessel 100 may occur as follows. A suitable amount of liquid, such as low-concentration (like 3% to 6%) hydrogen peroxide solution, can be placed in the volume 106 of the containment vessel 100. For instance, the amount of liquid may be adequate to cover the bottom surface of the interior volume 106 of the containment vessel 100 without being so high as to extend above the base 112 when the base 112 is placed into the interior volume 106. Also, a suitable amount of personal protection equipment 114 can be placed on the base 112, such as an amount of personal protection equipment 114 that partially or substantially fills the interior volume 106 of the containment vessel 100. The personal protection equipment 114 may or may not have been previously soaked in liquid, such as a low-concentration hydrogen peroxide solution. The base 112 can be placed into the interior volume 106 of the containment vessel 100 before or after the personal protection equipment 114 is placed on the base 112. The lid 104 can be secured to the body 102 of the containment vessel 100, and the containment vessel 100 can be heated (such as in a microwave, on a stovetop, in an oven, using solar radiation, or in any other suitable manner). The pressure-relief valve(s) of the integrated filter(s) and pressure-relief valve(s) 110 may initially be opened to allow air in the containment vessel 100 to be substantially replaced with vapor, and the pressure-relief valve(s) of the integrated filter(s) and pressure-relief valve(s) 110 may then be closed. The heating may then continue for a specified time period, such as between about five minutes to about ten minutes. The heating can heat the personal protection equipment 114 to a temperature within a relatively-low temperature range, such as about 65° C. to about 80° C., to prevent damage to the personal protection equipment 114.

Once this part of the process is completed, the personal protection equipment 114 can be dried, which may occur in any suitable manner. For instance, in some cases, the personal protection equipment 114 may be removed from the containment vessel 100 and allowed to air dry (such as on a rack), or the personal protection equipment 114 may be removed from the containment vessel 100 and mechanically dried using a hair dryer or other heat or air source. In other cases, the pressure-relief valve(s) of the integrated filter(s) and pressure-relief valve(s) 110 can be opened, and the containment vessel 100 can again be heated (possibly in the same or similar manner as the first heating) so that moisture within the containment vessel 100 can escape and allow drying of the personal protection equipment 114. Any other suitable approach for drying the personal protection equipment 114 may also be used here.

Note that rotation of the containment vessel 100 may or may not occur during heating, so the containment vessel 100 may be used in non-rotating microwaves or with other heat sources that lack rotation capabilities. Of course, nothing prevents the containment vessel 100 from being used in a microwave or with another heat source that includes rotation capabilities. However, the ability to support non-rotational use of the containment vessel 100 may allow larger or non-cylindrical versions of the containment vessel to be designed and used, since requiring rotation of the containment vessel may limit the maximum size of the containment vessel in certain applications (like with rotating microwaves). Also note that while the base 112 is described above as being placed over a liquid reservoir in the containment vessel 100, the base 112 may be integrated with or otherwise be used in conjunction with a pan under the base 112, where the pan holds liquid like a low-concentration hydrogen peroxide solution.

Although FIGS. 1 through 4 illustrate a first example of a containment vessel 100 for rapid thermo-chemical decontamination of facemasks or other personal protection equipment, various changes may be made to FIGS. 1 through 4. For example, the sizes, shapes, and dimensions of the containment vessel 100 and its individual components can vary as needed or desired. Also, the number and placement of various components of the containment vessel 100 can vary as needed or desired. In addition, the containment vessel 100 may be used in any other suitable decontamination process and is not limited to the specific processes described above.

Figure 5:
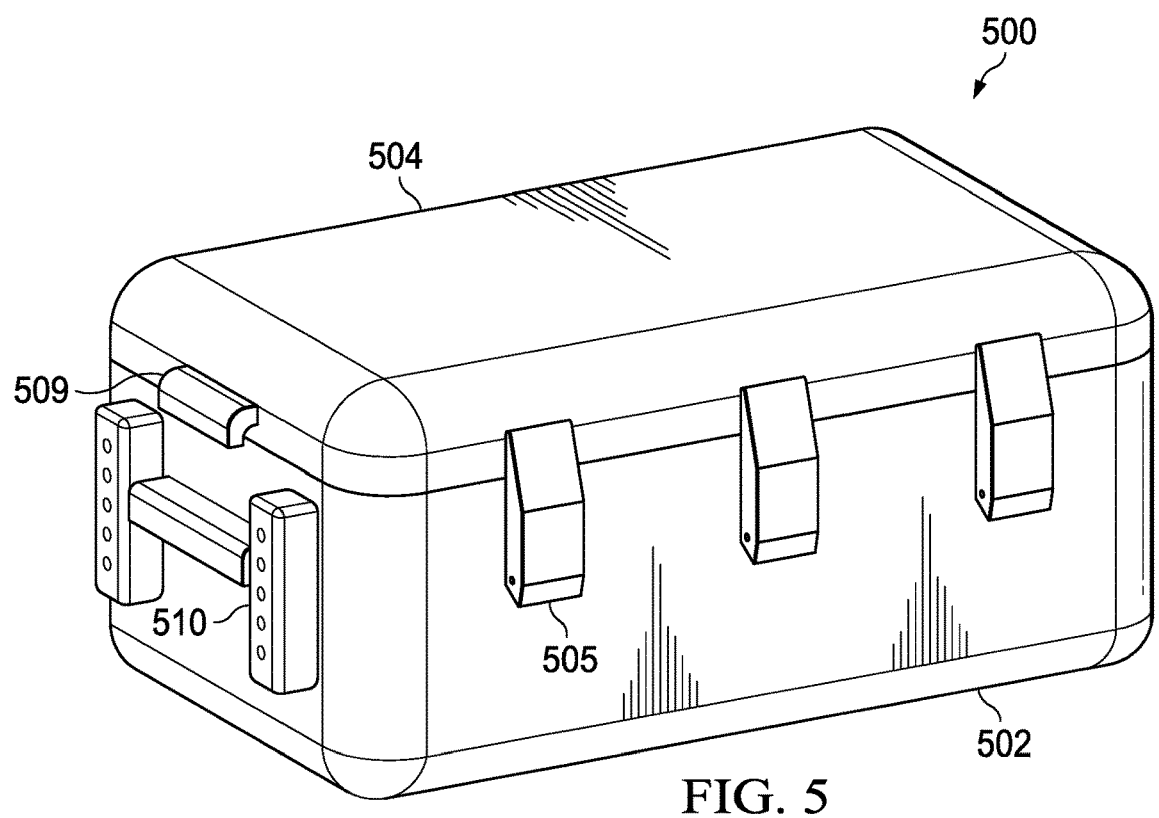
FIGS. 5 through 8 illustrate a second example containment vessel for rapid thermo-chemical decontamination of facemasks or other personal protection equipment in accordance with this disclosure.
Figure 6:
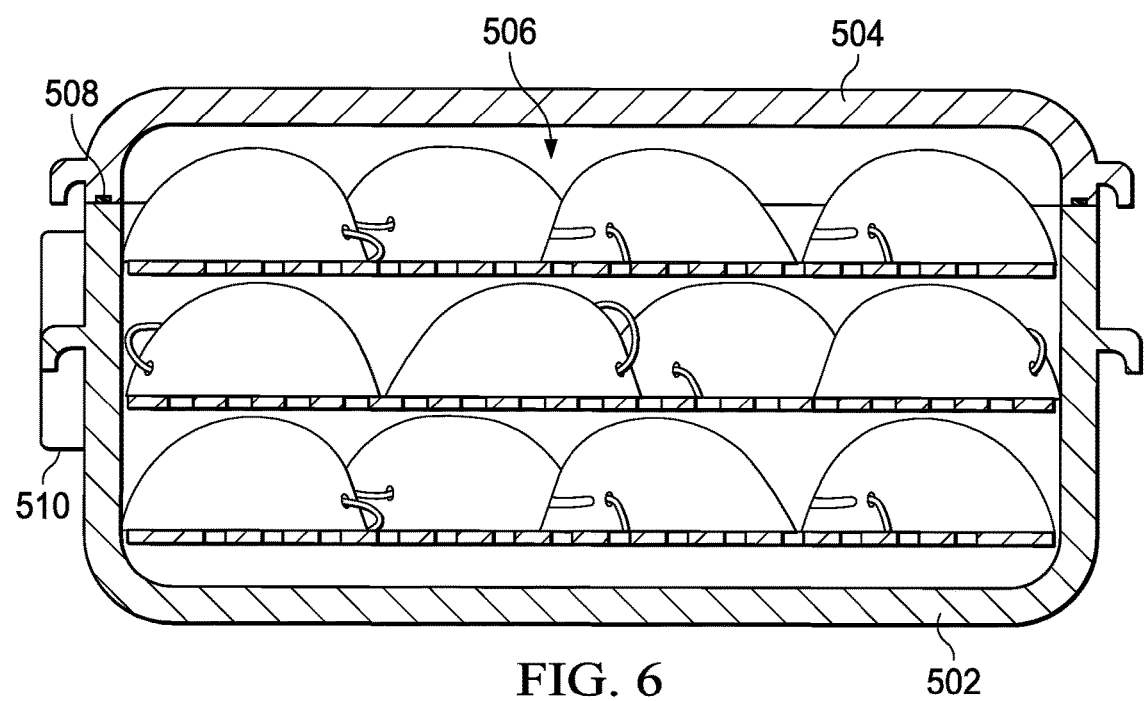

FIGS. 5 through 8 illustrate a second example containment vessel 500 for rapid thermo-chemical decontamination of facemasks or other personal protection equipment in accordance with this disclosure. As shown in FIGS. 5 and 6, the containment vessel 500 generally takes the form of a larger structure (relative to the containment vessel 100) that may be used in a commercial microwave or other larger heat source. In this example, the containment vessel 500 includes a body 502 and a lid 504 configured to be secured to the body 502. In this example, the lid 504 can be secured to the body 502 using a number of clamps 505, such as pivotable clamps that are attached to sides of the body 502 and that can be extended, attached to the lid 504, and retracted. The body 502 and lid 504 collectively define an interior space or volume 506 into which personal protection equipment can be placed. A seal 508 may be positioned between the body 502 and the lid 504 in order to help isolate or seal the volume 506 when the lid 504 is secured to the body 502. This helps to retain water, hydrogen peroxide, contaminants, or other materials inside the containment vessel 500 until a decontamination process is completed. The body 502 and/or the lid 504 may optionally include handles 509 to facilitate easier lifting or transport of the containment vessel 500.

The body 502 and lid 504 of the containment vessel 500 may be formed from any suitable material(s). In some embodiments, the body 502 and lid 504 may be formed from ruggedized plastic or other material(s) that can be used in a microwave. This may include one or more materials having a low loss tangent at 915 MHz and/or 2.45 GHz and a suitable glass transition or softening temperature, such as high-density polyethylene, polymethylpentene, polypropylene, or polysulfone. Other materials may include those normally used in food preparation, such as metal, tempered glass, or ceramic. The body 502 and lid 504 may also be formed in any suitable manner, such as additive manufacturing, injection molding, casting, machining, or other suitable technique. The containment vessel 500 overall may have any suitable size, shape, and dimensions, and each of the body 502 and lid 504 may have any suitable size, shape, and dimensions. In some cases, the containment vessel 500 may be sized and shaped to fit within a commercial microwave. The seal 508 includes any suitable structure configured to seal the interior space of the containment vessel 500, such as a rubber or other O-ring. Each clamp 505 includes any suitable structure configured to secure the lid 504 to the body 502. Note, however, that any other suitable mechanism may be used to secure the lid 504 to the body 502. Each handle 509 may be formed integral with the body 502/lid 504 or formed separate from and attached to the 502/lid 504.

One or more integrated filters and pressure-relief valves 510 can be used with the containment vessel 500. Each pressure-relief valve includes any suitable structure configured to be selectively opened and closed to provide or block a pathway for pressure to escape from the interior volume 506 of the containment vessel 500. Each filter may be used to filter air or other fluid passing out of the containment vessel 500, such as during or after heating of the containment vessel 500. For instance, after being placed in a microwave or otherwise heated for a specified period of time, the pressure-relief valve(s) may be opened, and the filter(s) may filter air passing out of the containment vessel 500. Among other things, this may help to prevent contamination of a microwave, stovetop, oven, or other components used with or around the containment vessel 500. Each filter includes any suitable structure configured to remove contaminants or other materials from fluid, such as a HEPA filter.

Note that this example includes two integrated filters and pressure-relief valves 510, although the containment vessel 500 may include one or more than two integrated filters and pressure-relief valves 510. Also note that the one or more integrated filters and pressure-relief valves 510 may be positioned at any suitable location(s) of the containment vessel 500 and may or may not be positioned on one or more sides of the body 502. Further note that the use of integrated filters and pressure-relief valves is not required and that, for instance, at least one pressure-relief valve and at least one separate filter may be used (or the filter or filters may be omitted completely).

Figure 7:
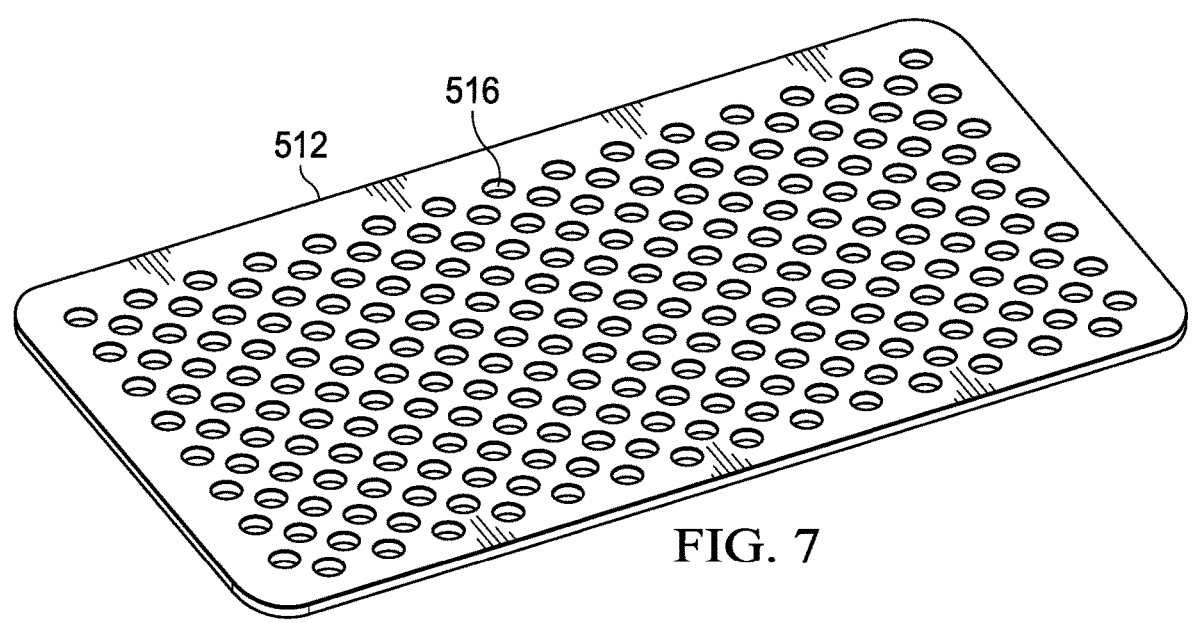
Figure 8:
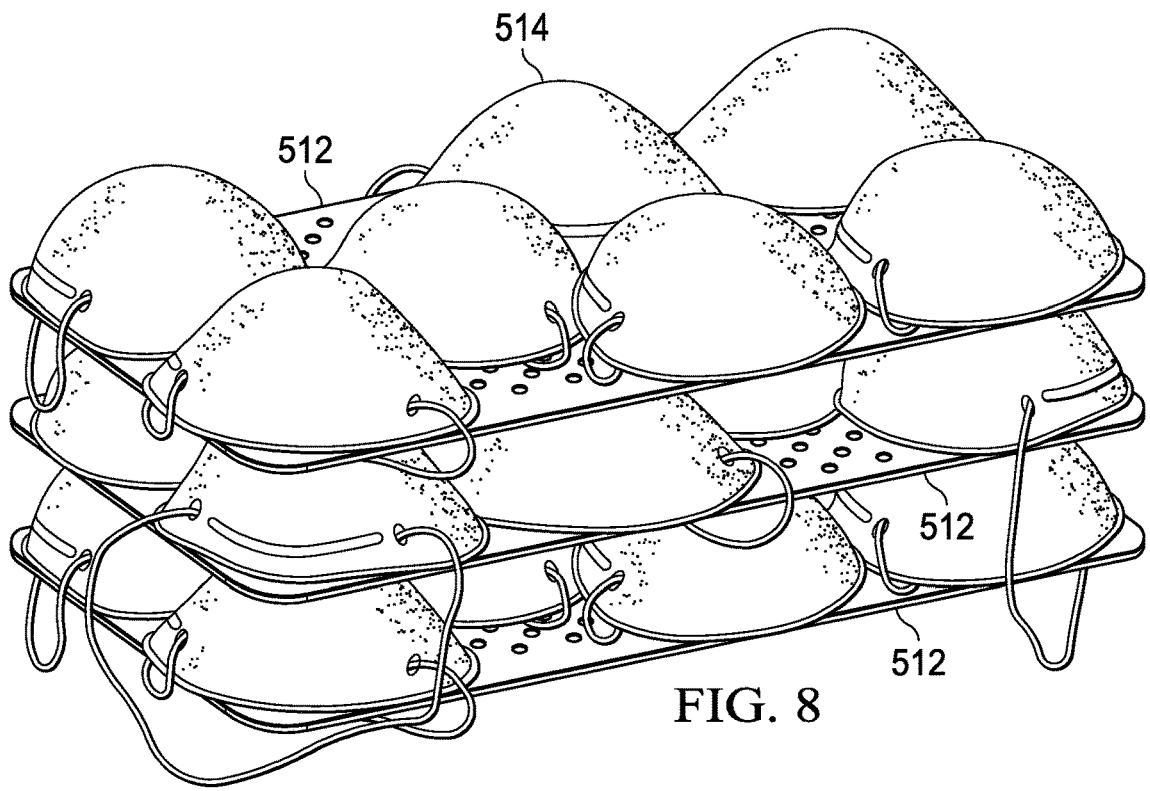

As shown in FIGS. 7 and 8, multiple bases 512 are sized and shaped to fit within the internal volume 506 in the containment vessel 500. Note that this example includes three bases 512, although the containment vessel 500 may include one, two, or more than three bases 512. Also note that the inner wall(s) of the internal volume 506 may be slanted, in which case the multiple bases 512 may have different sizes. One or more pieces of personal protection equipment 514 can be placed on each base 512, and each base 512 holds the personal protection equipment 514 above a bottom surface of the internal volume 506 or above a lower base 512. This allows a reservoir of liquid (such as a low-concentration hydrogen peroxide solution) to be placed within the internal volume 506 of the containment vessel 500 and remain underneath the lowest base 512. When the reservoir of liquid is heated, vaporized liquid can travel upward and surround the personal protection equipment 514 to facilitate decontamination of the personal protection equipment 514. In this example, each base 512 includes multiple holes 516, which allow vaporized liquid (such as hydrogen peroxide vapor) to travel from under the base 512 to surround the personal protection equipment 514 during the decontamination process.

Separation of the bases 512 from the bottom surface of the internal volume 506 or from one another when inserted into the containment vessel 500 may be achieved in any suitable manner. For example, in some embodiments, the lowest base 512 may be separated from the bottom surface of the internal volume 506 using standoffs (which may be the same as or similar to the standoffs 118 described above), and each higher base 512 may be separated from a lower base 512 using taller standoffs. In other embodiments, at least some of the bases 512 may rest on brackets that project inward from the inner wall(s) of the internal volume 506, and each lower base 512 may be sized or shaped to move past brackets for higher bases 512 or may include slots that allow that base 512 to pass around the brackets for higher bases 512. However, any other suitable mechanism may be used here to support or separate the bases 512.

Each base 512 may be formed from any suitable material(s), such as metal or ruggedized plastic. Each base 512 may also be formed in any suitable manner, such as additive manufacturing, injection molding, casting, machining, or other suitable technique. Each base 512 may have any suitable size, shape, and dimensions. In this example, each base 512 is generally rectangular with rounded corners, although other shapes may be used. Each of the holes 516 may have any suitable size, shape, and dimensions, and any suitable number and arrangement of the holes 516 may be used in each base 512. The holes 516 may also be formed in each base 512 in any suitable manner, such as by etching or otherwise forming the holes 516 in an already-formed base 512 or by forming each base 512 to include the holes 516.

In this example, the pieces of personal protection equipment 514 include multiple facemasks, such as N95, N99, N100, or P100 surgical masks. In this particular example, seven or eight facemasks can be placed on each base 512 in order to substantially or completely fill the interior volume 506 of the containment vessel 500. However, any other suitable arrangement of personal protection equipment 514 may be used here, including stacks of personal protection equipment 514 (which may or may not require removal of one or more of the bases 512 depending on the size of the containment vessel 500). The presence of the liquid reservoir (such as a reservoir of low-concentration hydrogen peroxide solution) under the bases 512 allows vapor to form and travel through the holes 516 of the bases 512 and surround the facemasks. The heating of the interior volume 506 of the containment vessel 500, along with the presence of the vaporized liquid around the personal protection equipment 514, helps to facilitate faster and more effective decontamination of the personal protection equipment 514.

In some embodiments, a decontamination process involving the containment vessel 500 may occur as follows. A suitable amount of liquid, such as low-concentration (like 3% to 6%) hydrogen peroxide solution, can be placed in the volume 506 of the containment vessel 500. For instance, the amount of liquid may be adequate to cover the bottom surface of the interior volume 506 of the containment vessel 500 without being so high as to extend above the lowest base 512 when that base 512 is placed into the interior volume 506. Also, a suitable amount of personal protection equipment 514 can be placed on each base 512, such as an amount of personal protection equipment 514 that partially or substantially fills the interior volume 506 of the containment vessel 500. The personal protection equipment 514 may or may not have been previously soaked in liquid, such as a low-concentration hydrogen peroxide solution. Each base 512 can be placed into the interior volume 506 of the containment vessel 500 before or after the personal protection equipment 514 is placed on the base 512. The lid 504 can be secured to the body 502 of the containment vessel 500, and the containment vessel 500 can be heated (such as in a microwave, on a stovetop, in an oven, using solar radiation, or in any other suitable manner). The pressure-relief valve(s) of the integrated filter(s) and pressure-relief valve(s) 510 may initially be opened to allow air in the containment vessel 500 to be substantially replaced with vapor, and the pressure-relief valve(s) of the integrated filter(s) and pressure-relief valve(s) 510 may then be closed. The heating may then continue for a specified time period, such as between about five minutes to about ten minutes. The heating can heat the personal protection equipment 514 to a temperature within a relatively-low temperature range, such as about 65° C. to about 80° C., to prevent damage to the personal protection equipment 514.

Once this part of the process is completed, the personal protection equipment 514 can be dried, which may occur in any suitable manner. For instance, in some cases, the personal protection equipment 514 may be removed from the containment vessel 500 and allowed to air dry (such as on a rack), or the personal protection equipment 514 may be removed from the containment vessel 500 and mechanically dried using a hair dryer or other heat or air source. In other cases, the pressure-relief valve(s) of the integrated filter(s) and pressure-relief valve(s) 510 can be opened, and the containment vessel 500 can again be heated (possibly in the same or similar manner as the first heating) so that moisture within the containment vessel 500 can escape and allow drying of the personal protection equipment 514. Any other suitable approach for drying the personal protection equipment 514 may also be used here.

While a single reservoir of liquid is described as being used here, multiple reservoirs of liquid may also be used. For instance, each of one or more of the bases 512 may be integrated with or otherwise be used in conjunction with a pan under the base 512, where the pan holds liquid like a low-concentration hydrogen peroxide solution. Also, note that rotation of the containment vessel 500 may or may not occur during heating, so the containment vessel 500 may be used in non-rotating microwaves or with other heat sources that lack rotation capabilities. Of course, nothing prevents the containment vessel 500 from being used in a microwave or with another heat source that includes rotation capabilities.

Although FIGS. 5 through 8 illustrate a second example of a containment vessel 500 for rapid thermo-chemical decontamination of facemasks or other personal protection equipment, various changes may be made to FIGS. 5 through 8. For example, the sizes, shapes, and dimensions of the containment vessel 500 and its individual components can vary as needed or desired. Also, the number and placement of various components of the containment vessel 500 can vary as needed or desired. In addition, the containment vessel 500 may be used in any other suitable decontamination process and is not limited to the specific processes described above.

Figure 9:
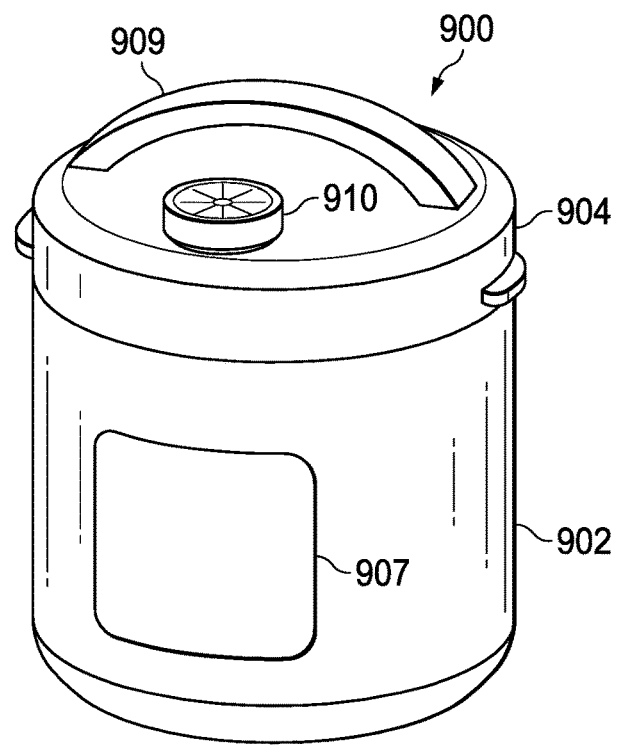
FIGS. 9 through 12 illustrate a third example containment vessel for rapid thermo-chemical decontamination of facemasks or other personal protection equipment in accordance with this disclosure.
Figure 10:
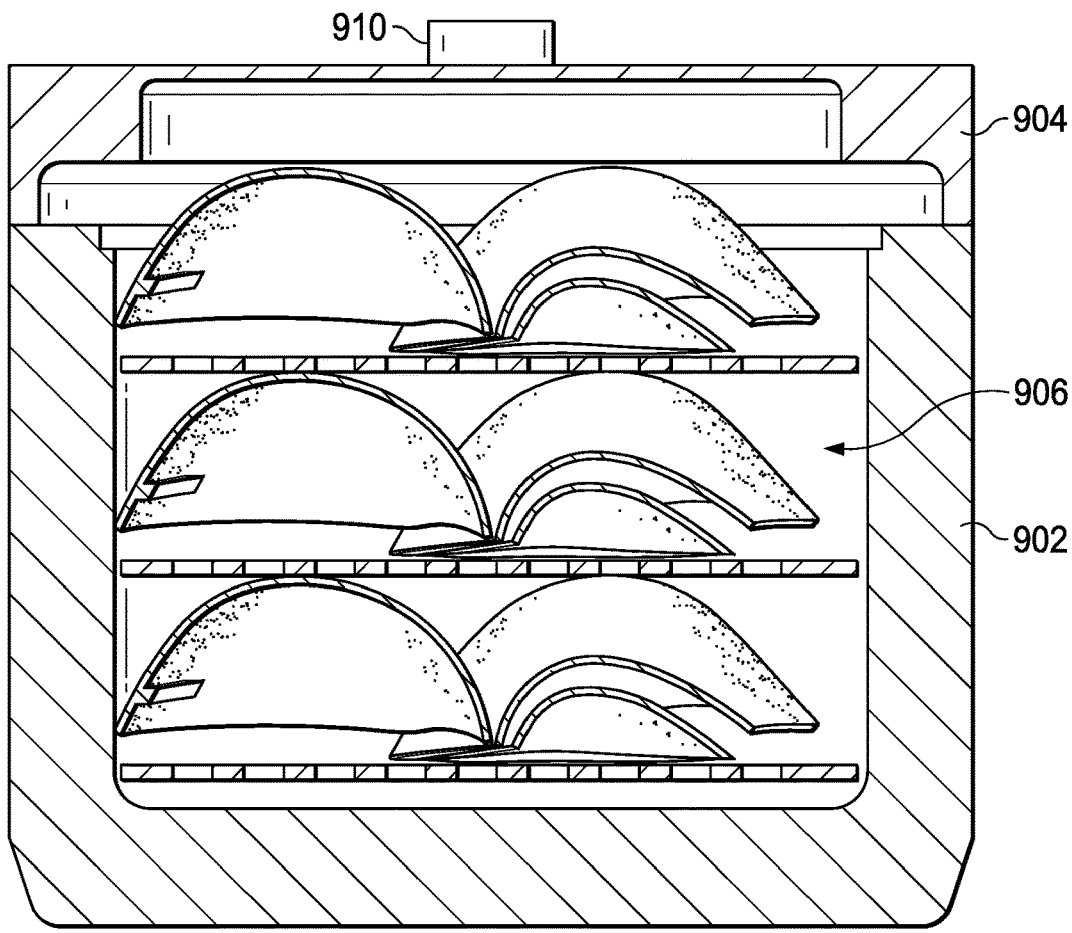

FIGS. 9 through 12 illustrate a third example containment vessel 900 for rapid thermo-chemical decontamination of facemasks or other personal protection equipment in accordance with this disclosure. As shown in FIGS. 9 and 10, the containment vessel 900 generally takes the form of a modified, customized, or other electronic pressure cooker or similar type of device. In this example, the containment vessel 900 includes a body 902 and a lid 904 configured to be secured to the body 902. The body 902 and lid 904 collectively define an interior space or volume 906 into which personal protection equipment can be placed. A seal (not shown) may be positioned between the body 902 and the lid 904 in order to help isolate or seal the volume 906 when the lid 904 is secured to the body 902. This helps to retain water, hydrogen peroxide, contaminants, or other materials inside the containment vessel 900 until a decontamination process is completed. Controls 907 (such as pressable buttons) may be provided to initiate and control the operation of the electronic pressure cooker, such as buttons for turning the pressure cooker on or off, controlling a temperature setting or duration of heating, and so on. The body 902 and/or the lid 904 may include one or more handles 909 to facilitate easier lifting or transport of the containment vessel 900.

The body 902 and lid 904 of the containment vessel 900 may be formed from any suitable material(s). In some embodiments, the body 902 and lid 904 may be formed from metal, ruggedized plastic, or other suitable materials. The body 902 and lid 904 may also be formed in any suitable manner. The containment vessel 900 overall may have any suitable size, shape, and dimensions, and each of the body 902 and lid 904 may have any suitable size, shape, and dimensions. As a particular example, the containment vessel 900 may have an internal volume 906 of about eight quarts, although other capacities may be used.

One or more integrated filters and pressure-relief valves 910 can be used with the containment vessel 900. Each pressure-relief valve includes any suitable structure configured to be selectively opened and closed to provide or block a pathway for pressure to escape from the interior volume 906 of the containment vessel 900. Each filter may be used to filter air or other fluid passing out of the containment vessel 900, such as during or after heating of the containment vessel 900. For instance, after heating equipment for a specified period of time, the pressure-relief valve(s) may be opened, and the filter(s) may filter air passing out of the containment vessel 900. Among other things, this may help to prevent contamination of a stovetop or other components used with or around the containment vessel 900. Each filter includes any suitable structure configured to remove contaminants or other materials from fluid, such as a HEPA filter.

Note that this example includes one integrated filter and pressure-relief valve 910, although the containment vessel 900 may include more than one integrated filter and pressure-relief valve 910. Also note that the one or more integrated filters and pressure-relief valves 910 may be positioned at any suitable location(s) of the containment vessel 900 and may or may not be positioned on the lid 904. Further note that the use of integrated filters and pressure-relief valves is not required and that, for instance, at least one pressure-relief valve and at least one separate filter may be used (or the filter or filters may be omitted completely).

Figure 11:
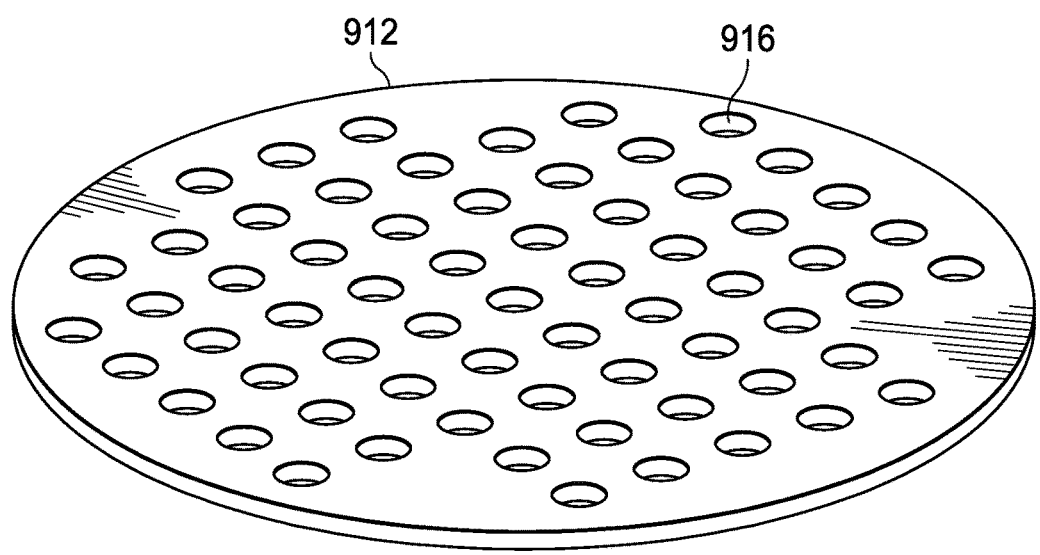
Figure 12:
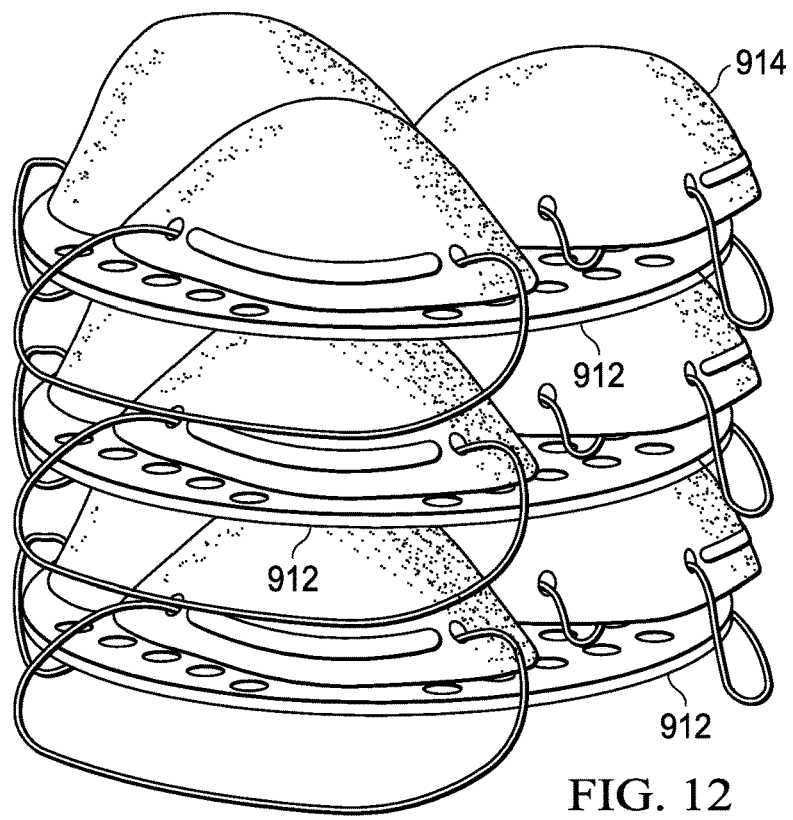

As shown in FIGS. 11 and 12, multiple bases 912 are sized and shaped to fit within the internal volume 906 in the containment vessel 900. Note that this example includes three bases 912, although the containment vessel 900 may include one, two, or more than three bases 912. Also note that the inner wall(s) of the internal volume 906 may be slanted, in which case the multiple bases 912 may have different sizes. One or more pieces of personal protection equipment 914 can be placed on each base 912, and each base 912 holds the personal protection equipment 914 above a bottom surface of the internal volume 906 or above a lower base 912. This allows a reservoir of liquid (such as a low-concentration hydrogen peroxide solution) to be placed within the internal volume 906 of the containment vessel 900 and remain underneath the lowest base 912. When the reservoir of liquid is heated, vaporized liquid can travel upward and surround the personal protection equipment 914 to facilitate decontamination of the personal protection equipment 914. In this example, each base 912 includes multiple holes 916, which allow vaporized liquid (such as hydrogen peroxide vapor) to travel from under the base 912 to surround the personal protection equipment 914 during the decontamination process.

Separation of the bases 912 from the bottom surface of the internal volume 906 or from one another when inserted into the containment vessel 900 may be achieved in any suitable manner. For example, in some embodiments, the lowest base 912 may be separated from the bottom surface of the internal volume 906 using standoffs (which may be the same as or similar to the standoffs 118 described above), and each higher base 912 may be separated from a lower base 912 using taller standoffs. In other embodiments, at least some of the bases 912 may rest on brackets that project inward from the inner wall(s) of the internal volume 906, and each lower base 912 may be sized or shaped to move past brackets for higher bases 912 or may include slots that allow that base 912 to pass around the brackets for higher bases 912. However, any other suitable mechanism may be used here to support or separate the bases 912.

Each base 912 may be formed from any suitable material(s), such as metal or ruggedized plastic. Each base 912 may also be formed in any suitable manner, such as additive manufacturing, injection molding, casting, machining, or other suitable technique. Each base 912 may have any suitable size, shape, and dimensions. In this example, each base 912 is generally circular, although other shapes may be used. Each of the holes 916 may have any suitable size, shape, and dimensions, and any suitable number and arrangement of the holes 916 may be used in each base 912. The holes 916 may also be formed in each base 912 in any suitable manner, such as by etching or otherwise forming the holes 916 in an already-formed base 912 or by forming each base 912 to include the holes 916.

In this example, the pieces of personal protection equipment 914 include multiple facemasks, such as N95, N99, N100, or P100 surgical masks. In this particular example, three facemasks can be placed on each base 912 in order to substantially or completely fill the interior volume 906 of the containment vessel 900. However, any other suitable arrangement of personal protection equipment 914 may be used here, including stacks of personal protection equipment 914 (which may or may not require removal of one or more of the bases 912 depending on the size of the containment vessel 900). The presence of the liquid reservoir (such as a reservoir of low-concentration hydrogen peroxide solution) under the bases 912 allows vapor to form and travel through the holes 916 of the bases 912 and surround the facemasks. The heating of the interior volume 906 of the containment vessel 900, along with the presence of the vaporized liquid around the personal protection equipment 914, helps to facilitate faster and more effective decontamination of the personal protection equipment 914.

In some embodiments, a decontamination process involving the containment vessel 900 may occur as follows. A suitable amount of liquid, such as low-concentration (like 3% to 6%) hydrogen peroxide solution, can be placed in the volume 906 of the containment vessel 900. For instance, the amount of liquid may be adequate to cover the bottom surface of the interior volume 906 of the containment vessel 900 without being so high as to extend above the lowest base 912 when that base 912 is placed into the interior volume 906. Also, a suitable amount of personal protection equipment 914 can be placed on each base 912, such as an amount of personal protection equipment 914 that partially or substantially fills the interior volume 906 of the containment vessel 900. The personal protection equipment 914 may or may not have been previously soaked in liquid, such as a low-concentration hydrogen peroxide solution. Each base 912 can be placed into the interior volume 906 of the containment vessel 900 before or after the personal protection equipment 914 is placed on the base 912. The lid 904 can be secured to the body 902 of the containment vessel 900, and the containment vessel 900 can heat the interior volume 906. The pressure-relief valve(s) of the integrated filter(s) and pressure-relief valve(s) 910 may initially be opened to allow air in the containment vessel 900 to be substantially replaced with vapor, and the pressure-relief valve(s) of the integrated filter(s) and pressure-relief valve(s) 910 may then be closed. The heating may then continue for a specified time period, such as between about five minutes to about ten minutes. The heating can heat the personal protection equipment 914 to a temperature within a relatively-low temperature range, such as about 65° C. to about 80° C., to prevent damage to the personal protection equipment 914.

Once this part of the process is completed, the personal protection equipment 914 can be dried, which may occur in any suitable manner. For instance, in some cases, the personal protection equipment 914 may be removed from the containment vessel 900 and allowed to air dry (such as on a rack), or the personal protection equipment 914 may be removed from the containment vessel 900 and mechanically dried using a hair dryer or other heat or air source. In other cases, the pressure-relief valve(s) of the integrated filter(s) and pressure-relief valve(s) 910 can be opened, and the containment vessel 900 can again heat the interior volume 906 so that moisture within the containment vessel 900 can escape and allow drying of the personal protection equipment 914. Any other suitable approach for drying the personal protection equipment 914 may also be used here.

While a single reservoir of liquid is described as being used here, multiple reservoirs of liquid may also be used. For instance, each of one or more of the bases 912 may be integrated with or otherwise be used in conjunction with a pan under the base 912, where the pan holds liquid like a low-concentration hydrogen peroxide solution.

Although FIGS. 9 through 12 illustrate a third example of a containment vessel 900 for rapid thermo-chemical decontamination of facemasks or other personal protection equipment, various changes may be made to FIGS. 9 through 12. For example, the sizes, shapes, and dimensions of the containment vessel 900 and its individual components can vary as needed or desired. Also, the number and placement of various components of the containment vessel 900 can vary as needed or desired. In addition, the containment vessel 900 may be used in any other suitable decontamination process and is not limited to the specific processes described above.

If needed or desired, at least one temperature sensor (such as an infrared sensor or temperature probe) may be used within any of the containment vessels 100, 500, 900 described above in order to measure the temperatures of the personal protection equipment within the containment vessel. The measured temperatures of the personal protection equipment may be fed back to a user or a control system in order to facilitate control of the power level, time, or other characteristics of the heating of the personal protection equipment. In some instances, this type of approach may be used with a customized microwave in which feedback from the temperature sensor(s) can be used to dynamically control the operation of the microwave. In other instances, the containment vessel itself may include temperature sensing and control functionality, such as when implemented using an electronic pressure cooker. In still other instances, an off-the-shelf microwave or other heat source may be used, and little or no feedback may be provided to the heat source (although feedback might be provided to a user or user device in some cases).

In various embodiments of the containment vessels 100, 500, 900 described above, a physical indicator may be used to identify when personal protection equipment in the containment vessel has been heated to a desired temperature range for a desired amount of time in order to complete a decontamination process. For example, a microwave-safe pop-up thermometer or other indicator (such as one similar to those used in turkeys to indicate when cooking is completed) may be incorporated into the containment vessel, and a red plastic cap or other component protrudes above the surface of the containment vessel when the desired temperature and time have been reached and decontamination has been completed. However, heating may occur without any visual or other feedback.

Various approaches may be used to calibrate a microwave or other heat source to ensure that personal protection equipment is heated to an appropriate temperature range and maintained there for a period needed to complete a decontamination process without overheating. In some cases, for example, test strips containing *Bacillus atrophaeus* spores or other contaminants can be placed on masks or other equipment that is placed inside a containment vessel, and heating of the masks or other equipment may occur using one or more specified settings of the heat source (such as power level and duration). This can be repeated for various settings of the heat source. The test strips can then be evaluated to identify which settings are adequate for decontamination, and the masks or other equipment can be inspected for damage. One or more suitable settings for decontaminating the masks or other equipment while avoiding damage to the equipment can then be identified. In other instances, a microwave or other heat source may be set to a relatively low power and activated for a prolonged period of time, and a user may constantly monitor a pop-up or other indicator and turn the heat source off when the indicator is triggered. In general, there are a number of ways in which conventional (non-customized) microwaves or other heat sources or customized microwaves or other heat sources can be used here.

Note that these various approaches are scalable and can support various implementations, such as rapid deployments using commercial microwaves to custom systems designed for high throughput. These approaches also allow local scaling, such as when hospitals or nursing homes leverage neighborhood restaurants to rapidly decontaminate personal protection equipment. Also note that while various personal protection equipment, including surgical facemasks, can be decontaminated using the approaches described here, particular types of personal protection equipment may be excluded from use in certain circumstances. For example, some facemasks use an active carbon filter layer or other active carbon filter element. These types of facemasks may not be decontaminated using microwave radiation from a microwave, as the active carbon in the filter element may combust. However, these types of facemasks may be decontaminated if heating is provided via another mechanism, such as stovetop, oven, or solar heating.

Figure 13:
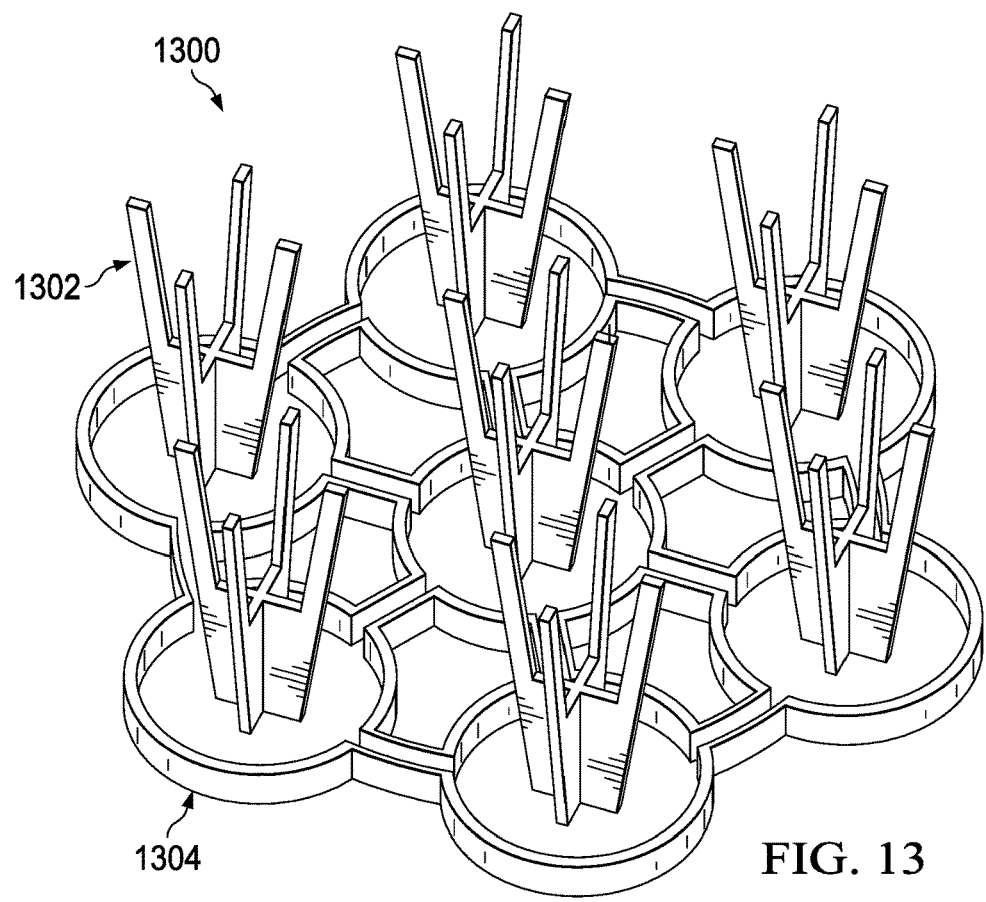
FIGS. 13 through 15 illustrate an alternative structure for holding facemasks or other personal protection equipment in a containment vessel during rapid thermo-chemical decontamination in accordance with this disclosure.
Figure 14:
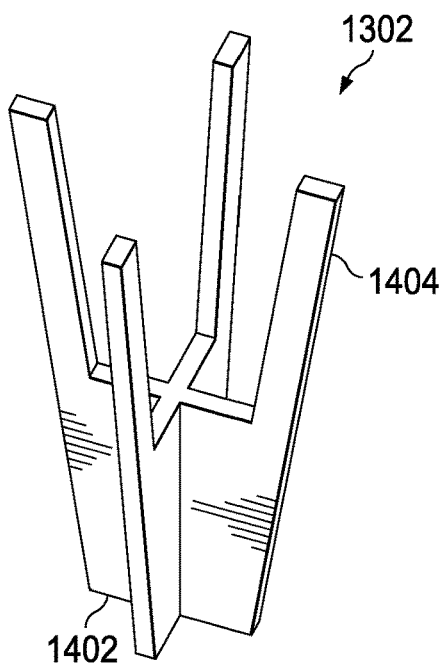
Figure 15:
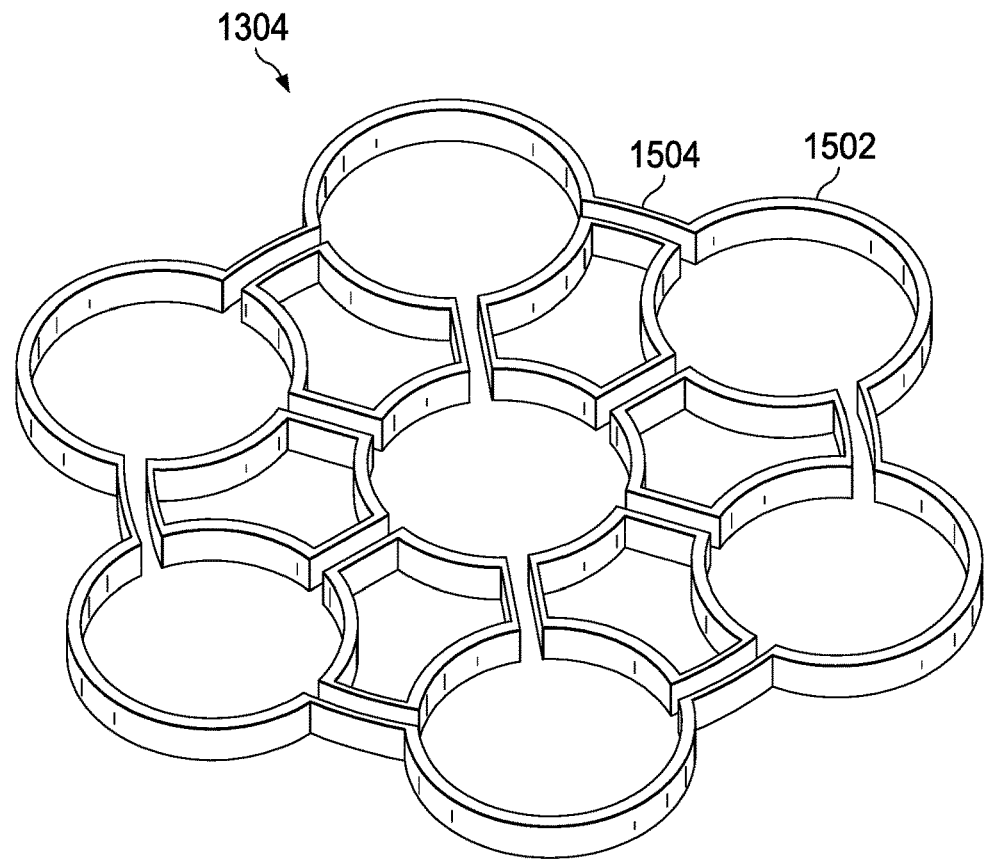

The containment vessels described above have been illustrated as using substantially flat or planar bases to hold masks or other personal protection equipment. However, non-planar bases may also be used in any of these containment vessels. The specific design of a non-planar base can vary as needed or desired. FIGS. 13 through 15 illustrate an alternative structure 1300 for holding facemasks or other personal protection equipment in a containment vessel during rapid thermo-chemical decontamination in accordance with this disclosure. As shown in FIG. 13, the structure 1300 includes multiple stands 1302 that extend upward. The stands 1302 are configured to receive and hold masks or other personal protection equipment above liquid. In some embodiments, the stands 1302 are spaced equally or substantially equally apart in order to maintain adequate and more uniform spacing between the equipment. The structure 1300 also includes a liquid holding area 1304 in which the multiple stands 1302 are placed and that holds the liquid (such as a low-concentration hydrogen peroxide solution).

As can be seen in FIG. 14, each stand 1302 includes a base portion 1402 and multiple arms 1404 extending upward from the base portion 1402. The base portion 1402 is configured to support the arms 1404, and the arms 1404 are configured to receive at least one piece of personal protection equipment to be decontaminated. In this particular example, the base portion 1402 has a cross-section in the form of a "+" sign, and each arm 1404 has a cross-section in the form of a rectangle. However, the base portion 1402 and arms 1404 may each have any other suitable cross-sectional shape. Also, while four arms 1404 extend upward from the base portion 1402 in this example, the stand 1302 may include any other suitable number of arms 1404.

As can be seen in FIG. 15, the liquid holding area 1304 includes multiple reservoirs 1502, each of which can be used to receive and hold liquid under personal protection equipment placed on one of the stands 1302. In this example, each reservoir 1502 has a generally circular shape, although each reservoir 1502 may have any other suitable shape. Also, there are eight reservoirs 1502 here (associated with eight stands 1302), although other numbers of stands 1302 and reservoirs 1502 may be used. Further, the layout and arrangement of the reservoirs 1502 here are for illustration only. Channels 1504 may optionally fluidly couple adjacent reservoirs 1502 so that liquid can travel between different reservoirs 1502 if needed. This may allow, for example, liquid in one reservoir 1502 to be replenished with liquid from another reservoir 1502 if the liquid vaporizes at different rates from the reservoirs 1502 during heating.

Note that while not shown here, the stands 1302 may be attached to the liquid holding area 1304 to support the stands 1302 and prevent the stands 1302 from falling over. In these embodiments, each stand 1302 may be attached to the liquid holding area 1304 at one or more locations, and the attachments may be positioned or designed so as to not interfere with or block the flow of liquid between the reservoirs 1502 through the channels 1504 (assuming the channels 1504 are present). Also note that while not shown here, the structure 1300 itself can be secured or otherwise attached to a lower base (such as a circular or rectangular base as described above). The lower base may be solid and lack holes so that liquid cannot escape from the reservoirs 1502.

The stands 1302 and the liquid holding area 1304 may be formed from any suitable material(s), such as metal or ruggedized plastic. The stands 1302 and the liquid holding area 1304 may also be formed in any suitable manner, such as additive manufacturing, injection molding, casting, machining, or other suitable technique. The stands 1302 and the liquid holding area 1304 may each have any suitable size, shape, and dimensions.

The structure 1300 shown here may be used in any of the containment vessels 100, 500, 900 described above or in other containment vessels designed in accordance with this disclosure. Depending on the size of the structure 1300 and the size of the containment vessel used, multiple instances of the structure 1300 may be stacked within the containment vessel.

Although FIGS. 13 through 15 illustrate one example of an alternative structure 1300 for holding facemasks or other personal protection equipment in a containment vessel during rapid thermo-chemical decontamination, various changes may be made to FIGS. 13 through 15. For example, the sizes, shapes, and dimensions of the components of the structure 1300 can vary as needed or desired. Also, the number and placement of various components of the structure 1300 can vary as needed or desired. In addition, the structure 1300 may be used in any other suitable decontamination process and is not limited to the specific processes described above.

It may be advantageous to set forth definitions of certain words and phrases used throughout this patent document. The terms "include" and "comprise," as well as derivatives thereof, mean inclusion without limitation. The term "or" is inclusive, meaning and/or. The phrase "associated with," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

The description in the present application should not be read as implying that any particular element, step, or function is an essential or critical element that must be included in the claim scope. The scope of patented subject matter is defined only by the allowed claims. Moreover, none of the claims invokes 35 U.S.C. § 112(f) with respect to any of the appended claims or claim elements unless the exact words "means for" or "step for" are explicitly used in the particular claim, followed by a participle phrase identifying a function.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure.

What is claimed is:

1. A method comprising:
    placing multiple reservoirs of liquid to be vaporized during a decontamination process in a liquid holding area in an interior space of a containment vessel, wherein the liquid holding area includes multiple channels fluidly coupling the reservoirs;
    transporting the liquid between the reservoirs using the multiple channels;
    placing multiple pieces of personal protection equipment within the interior space of the containment vessel on multiple stands of a base, the base configured to hold the pieces of personal protection equipment above the reservoirs of liquid;
    sealing the interior space of the containment vessel;
    vaporizing the liquid in the reservoirs to travel upward and surround the pieces of personal protection equipment by applying external heat to the containment vessel;
    decontaminating the pieces of personal protection equipment by heating the pieces of personal protection equipment in the sealed interior space of the containment vessel; and
    opening a pressure-relief valve of the containment vessel after decontaminating the pieces of personal protection equipment.

2. The method of claim 1, further comprising:
    drying the decontaminated pieces of personal protection equipment by heating the decontaminated pieces of personal protection equipment in the containment vessel after the pressure-relief valve is opened.

3. The method of claim 1, wherein the reservoirs of liquid comprise at least one reservoir of a low-concentration hydrogen peroxide solution.

4. The method of claim 1, wherein heating the pieces of personal protection equipment comprises heating the pieces of personal protection equipment to a temperature of about 65° C. to about 80° C.

5. The method of claim 1, further comprising:
    allowing the vaporized liquid to pass through multiple holes in the base and surround the pieces of personal protection equipment.

6. The method of claim 1, further comprising:
    filtering air or liquid material passing through the pressure-relief valve.

7. The method of claim 1, wherein heating the pieces of personal protection equipment comprises heating the pieces of personal protection equipment using a microwave, a stovetop, or an oven.

8. The method of claim 1, wherein:
    the base comprises one of multiple bases; and
    the method further comprises inserting each of the multiple bases into the interior space to receive one or more different pieces of personal protection equipment.

9. A method comprising:
    placing multiple reservoirs of liquid to be vaporized during a decontamination process in a liquid holding area in an interior space of a containment vessel, wherein the liquid holding area includes multiple channels fluidly coupling the reservoirs;
    transporting the liquid between the reservoirs using the multiple channels;
    placing multiple pieces of personal protection equipment within the interior space of the containment vessel on multiple stands of a first base, the first base configured to hold the pieces of personal protection equipment above the reservoirs of liquid;
    placing one or more additional pieces of personal protection equipment within the interior space of the containment vessel on a second base, the second base configured to hold the one or more additional pieces of personal protection equipment above the first base;
    sealing the interior space of the containment vessel;
    vaporizing the liquid in the reservoirs to travel upward and surround the pieces of personal protection equipment by applying external heat to the containment vessel;
    decontaminating the pieces of personal protection equipment and the one or more additional pieces of personal protection equipment by heating the pieces of personal protection equipment and the one or more additional pieces of personal protection equipment in the sealed interior space of the containment vessel; and
    opening a pressure-relief valve of the containment vessel after decontaminating the pieces of personal protection equipment and the one or more additional pieces of personal protection equipment.

10. The method of claim 9, further comprising:
    drying the decontaminated pieces of personal protection equipment and the one or more decontaminated additional pieces of personal protection equipment by heating the decontaminated pieces of personal protection equipment and the one or more decontaminated additional pieces of personal protection equipment in the containment vessel after the pressure-relief valve is opened.

11. The method of claim 9, wherein the reservoirs of liquid comprise at least one reservoir of a low-concentration hydrogen peroxide solution.

12. The method of claim 9, wherein heating the pieces of personal protection equipment and the one or more additional pieces of personal protection equipment comprises heating the pieces of personal protection equipment and the one or more additional pieces of personal protection equipment to a temperature of about 65° C. to about 80° C.

13. The method of claim 9, further comprising:
allowing the vaporized liquid to pass through multiple holes in the first base and surround the pieces of personal protection equipment.

14. The method of claim 9, further comprising:
filtering air or liquid material passing through the pressure-relief valve.

15. The method of claim 9, wherein heating the pieces of personal protection equipment and the one or more additional pieces of personal protection equipment comprises heating the pieces of personal protection equipment and the one or more additional pieces of personal protection equipment using a microwave, a stovetop, or an oven.

16. The method of claim 9, wherein the first base is sized or shaped to move past brackets for the second base.

17. The method of claim 1, wherein sealing the interior space of the containment vessel comprises closing the pressure-relief valve of the containment vessel once air in the interior space is replaced substantially with the vaporized liquid.

18. The method of claim 1, further comprising:
after opening the pressure-relief valve, heating an inside of the containment vessel to remove moisture from the pieces of personal protection equipment.

19. The method of claim 9, wherein sealing the interior space of the containment vessel comprises closing the pressure-relief valve of the containment vessel once air in the interior space is replaced substantially with the vaporized liquid.

20. The method of claim 9, further comprising:
after opening the pressure-relief valve, heating an inside of the containment vessel to remove moisture from the pieces of personal protection equipment.

* * * * *

UNITED STATES PATENT AND TRADEMARK OFFICE
CERTIFICATE OF CORRECTION

| | | |
|---|---|---|
| PATENT NO. | : 12,194,181 B2 | Page 1 of 1 |
| APPLICATION NO. | : 16/944617 | |
| DATED | : January 14, 2025 | |
| INVENTOR(S) | : Crouch et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 358 days.

Signed and Sealed this
Eighth Day of July, 2025

Coke Morgan Stewart
*Acting Director of the United States Patent and Trademark Office*